(12) United States Patent
Pathi et al.

(10) Patent No.: US 7,799,928 B2
(45) Date of Patent: Sep. 21, 2010

(54) PROCESS FOR THE PREPARATION OF IRBESARTAN HYDROCHLORIDE

(75) Inventors: Srinivas Laxminarayan Pathi, Bangalore (IN); Jayamadhava P. Relekar, Bangalore (IN); Dharmaraj Ramachandra Rao, Mumbai (IN); Rajendra Narayanrao Kankan, Mumbai (IN)

(73) Assignee: Cipla Limited, Mumbai (IN)

( * ) Notice: Subject to any disclaimer, the term of this patent is extended or adjusted under 35 U.S.C. 154(b) by 383 days.

(21) Appl. No.: 11/718,059

(22) PCT Filed: Oct. 26, 2005

(86) PCT No.: PCT/GB2005/004151

§ 371 (c)(1),
(2), (4) Date: Jul. 20, 2007

(87) PCT Pub. No.: WO2006/046043

PCT Pub. Date: May 4, 2006

(65) Prior Publication Data

US 2009/0137648 A1 May 28, 2009

(30) Foreign Application Priority Data

Oct. 26, 2004 (GB) .................... 0423746.7

(51) Int. Cl.
C07D 257/00 (2006.01)
C07D 403/00 (2006.01)
(52) U.S. Cl. .................. 548/147; 548/196; 548/201
(58) Field of Classification Search ............ 548/147, 548/196, 201
See application file for complete search history.

(56) References Cited

U.S. PATENT DOCUMENTS

| 5,270,317 | A | * | 12/1993 | Bernhart et al. ............. 514/269 |
| 5,541,209 | A | | 7/1996 | Spinale |
| 5,559,233 | A | | 9/1996 | Bernhart et al. |
| 5,629,331 | A | | 5/1997 | Caron et al. |
| 6,800,761 | B1 | | 10/2004 | Franc et al. |

FOREIGN PATENT DOCUMENTS

| AU | 641005 | 9/1993 |
| EP | 0454511 | 10/1991 |
| WO | WO9967236 | 12/1999 |
| WO | WO 03/050110 A1 | 6/2003 |
| WO | WO 2004/007482 A2 | 1/2004 |
| WO | WO 2004/072064 A1 | 8/2004 |

OTHER PUBLICATIONS

Foreign communication from a counterpart application—International Search Report and Written Opinion, PCT/GB2005/004151, Jan. 17, 2006, 12 pgs.
Foreign communication from a related counterpart application—International Preliminary Report on Patentability, PCT/GB2005/004151, Dec. 28, 2006, 20 pgs.

* cited by examiner

Primary Examiner—Susannah Chung
(74) Attorney, Agent, or Firm—Conley Rose, P.C.; Rodney B. Carroll

(57) ABSTRACT

The present invention is concerned with a process for the preparation of 2n-butyl-4-spirocyclopentane-1-[(2'-(tetrazol-5-yl)biphenyl-4-yl)methyl]-2-imidazolin-5-one hydrochloride, irbesartan hydrochloride, novel hydrated and anhydrous crystalline forms thereof, amorphous irbesartan hydrochloride, formulations containing the same, therapeutic uses thereof and methods of treatment employing the same. The process of the present invention is a one-pot process which comprises reacting intermediate compounds 2n-butyl-1,3-diazaspiro[4,4]non-1-en-4-one and 5-(4'-bromomethyl-biphenyl-2-yl)-1-trityl-1H-tetrazole.

40 Claims, 8 Drawing Sheets

PROCESS FOR THE PREPARATION OF IRBESARTAN HYDROCHLORIDE

CROSS-REFERENCE TO RELATED APPLICATIONS

This application is a filing under 35 U.S.C. 371 of International Application No. PCT/GB2005/004151 filed Oct. 26, 2005, entitled "Process for the Preparation of Irbesartan Hydrochloride," claiming priority of Great Britain Patent Application No. 0423746.7 filed Oct. 26, 2004, which applications are incorporated by reference herein in their entirety.

FIELD OF THE INVENTION

The present invention is concerned with a process for the preparation of 2n-butyl-4-spirocyclopentane-1-[(2'-(tetrazol-5-yl)biphenyl-4-yl)methyl]-2-imidazolin-5-one hydrochloride, irbesartan hydrochloride, novel crystalline forms thereof, formulations containing the same, therapeutic uses thereof and methods of treatment employing the same.

BACKGROUND OF THE INVENTION

Irbesartan, 2n-butyl-4-spirocyclopentane-1-[(2'-(tetrazol-5-yl)biphenyl-4-yl)methyl]-2-imidazolin-5 one, can be represented by the following structural formula

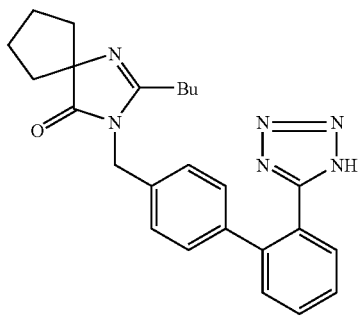

Irbesartan is a non-peptide angiotensin-II antagonist. Irbesartan inhibits the action of angiotensin—II on its receptor and thus prevents the increase in blood pressure produced by the hormone—receptor interaction. Irbesartan is, therefore, employed in the treatment of cardiovascular complaints, such as hypertension and heart failure.

U.S. Pat. No. 5,270,317 discloses certain N-substituted heterocyclic derivatives, including 2n-butyl-4-spirocyclopentane-1-[(2'-(tetrazol-5-yl)biphenyl-4-yl)methyl]-2-imidazolin-5 one, and methods of making and using the same.

U.S. Pat. No. 5,629,331 discloses two polymorphic forms, Form A and Form B, of 2n-butyl-4-spirocyclopentane-1-[(2'-(tetrazol-5-yl)biphenyl-4-yl)methyl]-2-imidazolin-5 one, a process for the preparation thereof and uses of the same for the treatment of hypertension.

WO 99/67236 discloses a new crystalline habit of Form A of 2n-butyl-4-spirocyclopentane-1-[(2'-(tetrazol-5-yl)biphenyl-4-yl)methyl]-2-imidazolin-5 one, a process for the preparation thereof and composition containing the same.

WO 03/050110$A_1$ discloses preparation of amorphous 2n-butyl-4-spirocyclopentane-1-[(2'-(tetrazol-5-yl)biphenyl-4-yl)methyl]-2-imidazolin-5 one from Form A and Form B.

WO 04/007482$A_2$ discloses a two phase preparation of irbesartan using a phase transfer catalyst at the trityl irbesartan stage.

WO 04/072064A1 discloses a number of processes for preparing irb-Tr, including reaction of the following starting materials in the presence of a phase transfer catalyst, an inorganic base and a solvent.

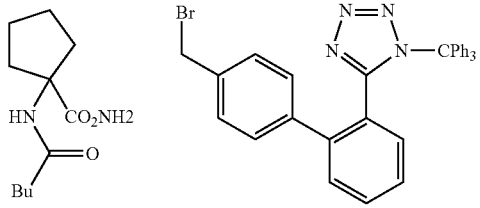

The WO2004/072064 process involves isolation of irb-Tr (by separation, column chromatography and, optionally, distillation) before conversion to irbesartan.

There is, however, a need for an improved process for the preparation of irbesartan for the following reasons.

The synthesis of irbesartan as discussed in U.S. Pat. No. 5,270,317, U.S. Pat. No. 5,559,233 and EP 0454511B involves a pre-penultimate reaction step (excluding workup and purification) which comprises reaction of a cyano group on the biphenyl ring with an azide, for example, tributyl tin azide. Reaction times as long as 210 hours are required, see line 5, column 20 of U.S. Pat. No. 5,270,317 and it is recognized in the art that there are safety risks associated with the use of azides.

U.S. Pat. No. 5,629,331 also discloses the reaction of an azide with a cyano group as above, the process being carried out in the presence of a dipolar aprotic solvent, for example, methylpyrrolidone, which is relatively high boiling and can be difficult to remove. U.S. Pat. No. 5,629,331 acknowledges safety risks involved in use of azides at high temperature (see column 4, line 39).

WO Patent 04/007482$A_2$ discloses the preparation of irbesartan using trityl irbesartan in a two phase reaction. Trityl irbesartan is first prepared, isolated in residue form and then detritylated in an acetone —HCl mixture, further basified, filtered with tritanol and reacidified to isolate irbesartan. The isolation of crude irbesartan involves basification, reacidification, toluene distillation and isolation, making the process tedious and unsuitable for use on an industrial scale.

Furthermore, formulation of irbesartan prepared by the above-described prior art processes has required much care because the resulting irbesartan powder tends to stick to the walls of equipment, for example, to the sides of the punches or to the mixer walls, due to its high electrostaticity. There is, therefore, a need for an improved process for the preparation of irbesartan, in particular a process that can provide irbesartan which is non-static, has free flowing properties, shorter reaction time and workup operations, and involves a simplified finishing operation which will enhance productivity and better intrinsic dissolution. This is now essentially achieved by a one-pot process according to the present invention, which results in irbesartan hydrochloride which has excellent flow properties.

SUMMARY OF THE INVENTION

According to the present invention, therefore, there is provided a one-pot process for the preparation of irbesartan hydrochloride of formula (I)

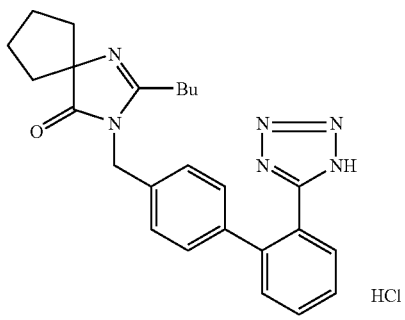

(I)

which one-pot process comprises reacting intermediate compounds 2n-butyl-1,3-diazaspiro[4,4]non-1-en-4-one of formula (II), optionally in salt form, preferably hydrochloride, and 5-(4'-bromomethyl-biphenyl-2-yl)-1-trityl-1H-tetrazole of formula (III)

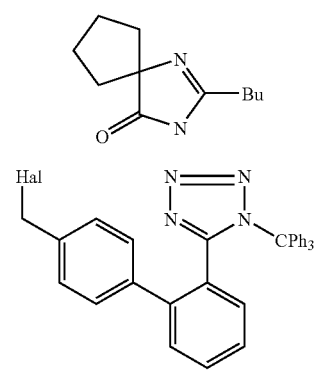

(II)

(III)

where Hal represents bromo, chloro, fluoro or iodo, preferably bromo. Intermediate compounds of formulae (II) and (III) are known in the art.

Reaction of intermediate compounds of formulae (II) and (III) results in formation of intermediate compound 2n-butyl-3-[2'(triphenyl methyl tetrazol-5yl)-biphenyl-4-yl-methyl]-1,3-diazaspiro[4,4]non-1-en-4-one of formula (IV) shown below, optionally in salt form, preferably hydrochloride, which is subsequently detritylated to yield irbesartan hydrochloride of formula (I)

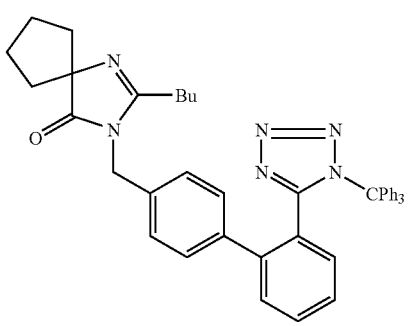

(IV)

A one-pot process for the preparation of irbesartan hydrochloride according to the present invention can thus be represented by the following reaction scheme

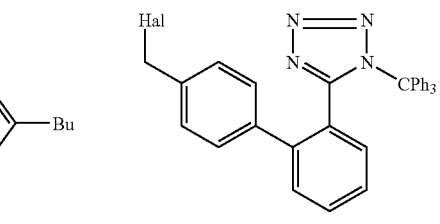

(II)          (III)

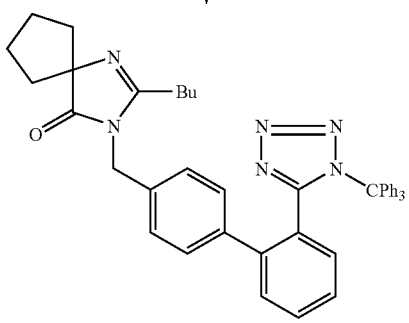

(IV)

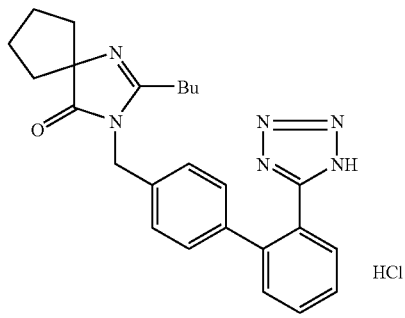

(I)

where Hal represents bromo, chloro, fluoro or iodo, preferably bromo, and each of intermediate compounds (II) and (IV) can optionally be present in salt form, preferably the hydrochloride.

A one-pot process according to the present invention can provide irbesartan hydrochloride in crystalline hydrated or anhydrous form, or in amorphous form, with high purity and yield, and which is free flowing, non-sticky and non-electrostatic. Preferably a one-pot process according to the present invention provides irbesartan hydrochloride as the sesquihydrate, hemihydrate, anhydrous or amorphous form, and also the process can be used for preparation of irbesartan free base either as Form A or Form B.

Typically an intermediate compound of formula (II) is employed in salt form, preferably the hydrochloride.

A one-pot process according to the present invention is preferably carried out in the presence of a phase transfer catalyst in a reaction system optionally comprising first and second phases, and also in the presence of an inorganic base. Detritylation is preferably achieved by using a mineral acid.

Use of phase transfer catalysts for a similar type of reaction has previously been described for preparation of angiotensin II receptor antagonist losartan. Phase transfer catalysts are of particular utility when at least first and second reactants have such different solubility characteristics that there is no practical common solvent therefor and accordingly combining a solvent for one with a solvent for the other results in a two phase system. Several classes of compounds are known to be capable of acting as phase transfer catalysts, for example, quaternary ammonium compounds, quaternary phosphonium compounds, crown ethers or the like.

BRIEF DESCRIPTION OF THE DRAWINGS

With reference to the Figures, these are as follows.

DETAILED DESCRIPTION OF THE INVENTION

Figure 1:
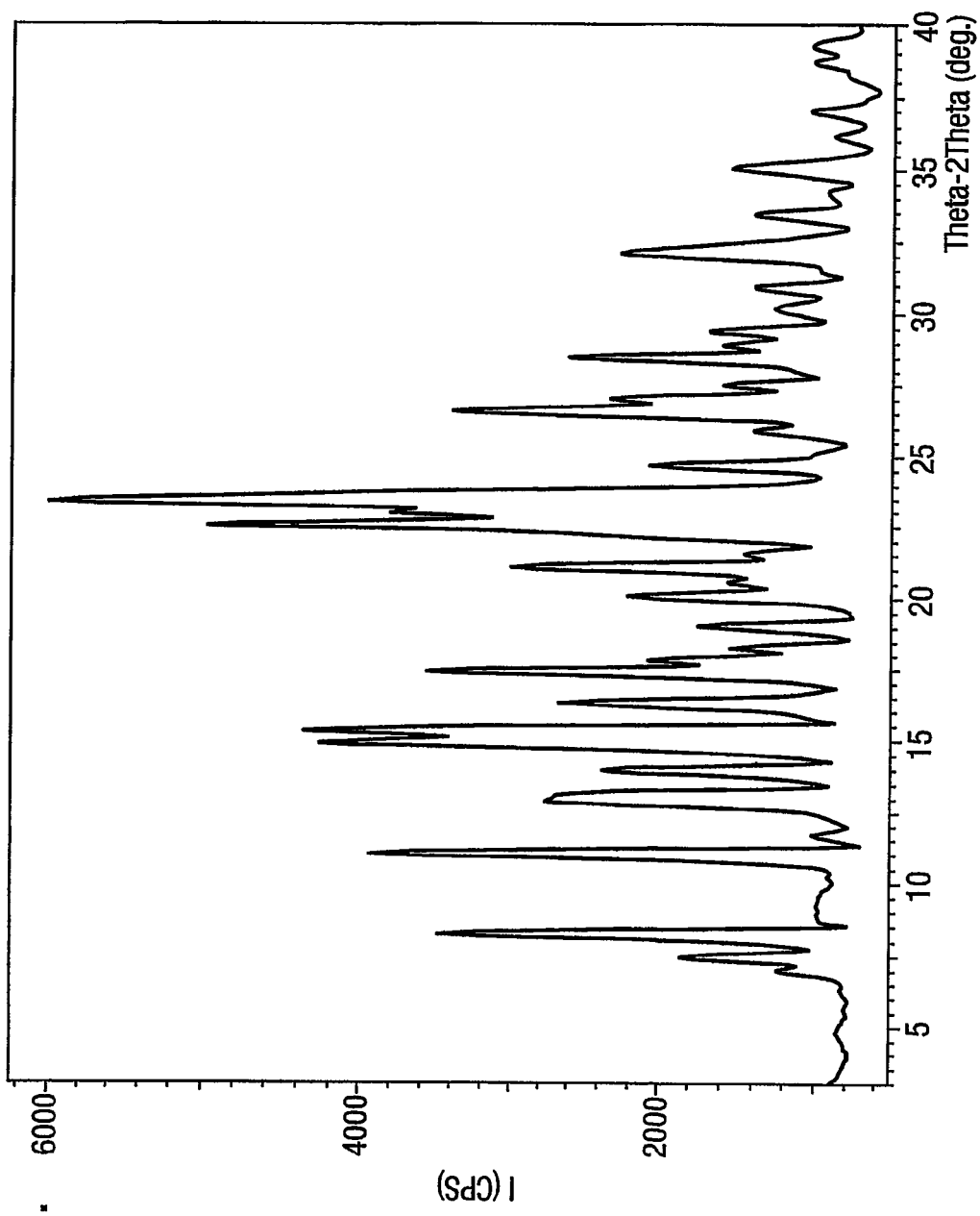
FIG. 1: An XRPD of irbesartan hydrochloride sesquihydrate according to the present invention obtained by using a Rigaku Miniflex between 20 to 40°.

A process according to the present invention preferably employs an aromatic or aliphatic hydrocarbon as a solvent of the one-pot reaction system, with a preferred solvent being an aromatic hydrocarbon, such as benzene, toluene, o-xylene, m-xylene, or the like. Toluene is a particularly preferred such aromatic hydrocarbon for use in accordance with the present invention. Aliphatic ketones, such as acetone and MIBK, may also be used as the solvent of the reaction system. Other hydrocarbons useful in the practice of the present invention will be apparent to the skilled artisan.

The solvent employed in a one-pot reaction system in a process according to the present invention can consist essentially of a hydrocarbon solvent substantially as described above. Alternatively, it may be preferred that the reaction system comprises first and second solvent phases. Suitably, the first solvent phase comprises a hydrocarbon solvent substantially as described above, and the solvent of the second solvent phase is substantially immiscible therewith. Typically, the solvent of the second solvent phase comprises water, which can be used alone, or more preferably an inorganic base can be combined therewith.

An inorganic base used in a reaction system according to the present invention can be selected from the group consisting of hydroxides, carbonates or alkoxides of alkali metals, such as for example KOH, NaOH, LiOH, $K_2CO_3$, $Na_2CO_3$, $Cs_2CO_3$, sodium methoxide, sodium t-butoxide, potassium t-butoxide and the like. An inorganic base for use in accordance with the present invention can be combined with water as the solvent of the second phase of the reaction system as described above or can be used as such in powdered form. The preferred base for use in a one-pot reaction according to the present invention is NaOH, potassium-t-butoxide or sodium-t-butoxide.

A synthetic one-pot process as provided by the present invention preferably involves the preparation of 2n-butyl-3-[2'(triphenyl methyl tetrazol-5yl)-biphenyl-4-yl-methyl]-1,3-diazaspiro[4,4]non-1-en-4-one hydrochloride of formula (IV) as shown above by the reaction of 5-(4'-bromomethyl biphenyl-2-yl)-1-trityl-1H-tetrazole of formula (III) and 2n-butyl-1,3-diazaspiro[4,4]-non-1-en-4-one of formula (II) as the HCl in presence of a base, with a phase transfer catalyst, in the presence of a hydrocarbon solvent, preferably toluene, optionally in presence of water as a second phase of the one-pot reaction system. The condensation of intermediate compounds of formulae (II) and (III) is preferably carried out at a temperature from about 20° C. to about 95° C., preferably at about 85° C. The reaction is allowed to proceed for a time that the skilled artisan will know to adjust according to the reaction temperature. For example, when the reaction temperature is about 90° C., a reaction time of between about 1 and 2 hours is usually sufficient. The reaction can be easily monitored using Thin Layer Chromatography. After reaction completion, the reaction is cooled to about 25° C. and the aqueous layer, if present, is separated, the reaction mass is washed with water and the layers are separated. A suitable acid, such as HCl (4N) is added to the reaction mass and stirred at about 55° C. for 40 minutes to 1 hour. The reaction can again be easily monitored by Thin Layer Chromatography and after reaction completion, the product can be filtered. Upon filtration, the product is washed with water and dried to yield irbesartan hydrochloride in hydrated form.

Optionally, the irbesartan hydrochloride according to the present invention can be purified further by dissolving in a solvent, such as methanol, at elevated temperatures and precipitated with a non-solvent, such as ethyl acetate. Irbesartan hydrochloride according to the present invention may also be purified by suspending in a solvent, such as ethyl acetate, isopropyl acetate or ethyl acetate-methanol mixture, at elevated temperatures and filtering the suspension at room temperature. The water of hydration is retained by the irbesartan hydrochloride in the above described processes of purification.

A process according to the present invention may further optionally comprise converting irbesartan hydrochloride prepared thereby to irbesartan free base, either Form A or Form B. Suitably the process can thus further comprise addition of a base, such as aqueous ammonia, to adjust the pH to about 6 to 7, followed by isolation of irbesartan free base either as Form A or Form B. The present invention further provides irbesartan free base, either Form A or Form B, prepared from a process as described herein.

In a one-pot process according to the present invention, isolation of trityl irbesartan is avoided and tedious work-up procedures such as distillation, basifying the reaction mass, and acidifying, as mentioned in Patent WO 04/007482, are not involved. In accordance with an especially advantageous embodiment of the invention, the two steps of coupling and hydrolysis are done using the same solvent and as such there is no replacing of one solvent with another. The above feature of the present invention eliminates the tedious process of distillation and thus avoids formation of impurities that are a feature of prior art processes. In another embodiment of the present invention, tritanol, which is a by-product of the reaction, is dissolved in toluene after detritylation and hence irbesartan can be directly filtered in a pure hydrochloride form. The present invention thus avoids filtration of tritanol and the whole process is completed in a single pot, without the need to isolate trityl irbesartan.

Thus, advantageously, the step of forming the trityl irbesartan and the steps of converting the trityl irbesartan to irbesartan is carried out in the same solvent or solvents. Advantageously, the step of converting the irbesartan to irbesartan hydrochloride is carried out in the same solvent or solvents as the earlier step(s).

Moreover, in this one-pot reaction the total time required to isolate irbesartan is about 8-10 hours, compared to the prior art processes that require a much longer time thus leading to a huge gain in productivity in accordance with the present invention. Hydrated irbesartan hydrochloride or anhydrous irbesartan hydrochloride obtained by the present invention is free flowing, less electrostatic, non-sticky, non-hygroscopic, has better intrinsic dissolution and is obtained in increased yield and purity.

According to the present invention, there is further provided crystalline hydrated and anhydrous irbesartan hydrochloride, which is substantially non-hygroscopic and has good flow characteristics as referred to above. There is further provided by the present invention crystalline irbesartan hydrochloride in hydrated form or anhydrous form as prepared by a process according to the present invention. Hydrates of irbesartan hydrochloride according to the present invention have a moisture content ranging from 1% to about 10% by weight and the anhydrous form of irbesartan hydrochloride has a moisture content ranging from 0.1 to 1.0% by weight. The present invention further provides irbesartan hydrochloride in amorphous form.

Specifically, therefore, the present invention discloses the amorphous, anhydrous, hemihydrate and sesquihydrate forms of irbesartan hydrochloride.

Figure 2:
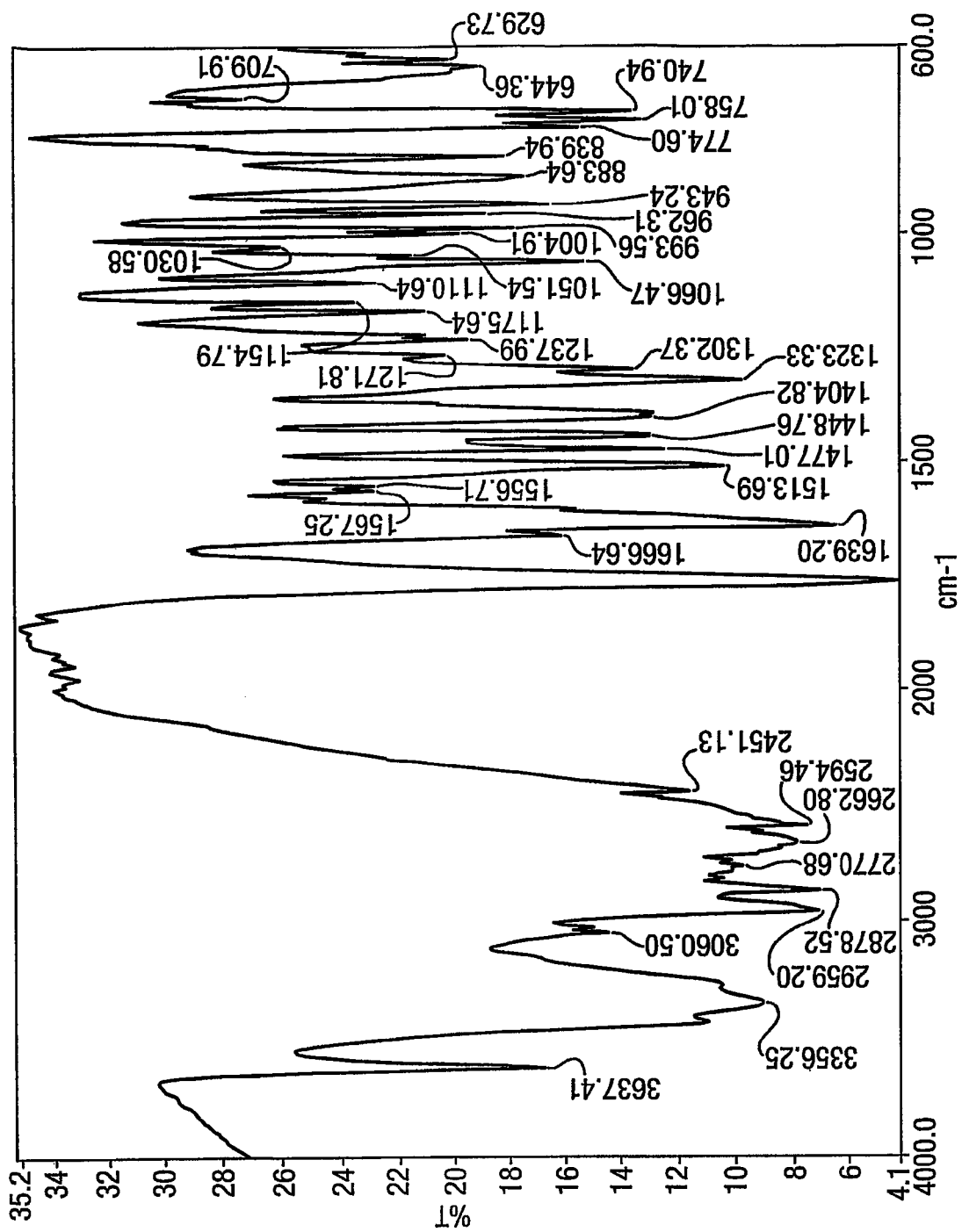
FIG. 2: An IR pattern of irbesartan hydrochloride sesquihydrate obtained by using a Parkin Elmer Paragon 500 Model.

There is provided by the present invention, therefore, crystalline irbesartan hydrochloride sesquihydrate having an IR pattern, or substantially the same IR pattern, as shown in FIG. 2. More particularly, irbesartan hydrochloride sesquihydrate has characteristic IR absorbance at about 3638, 3273, 2451, 1761, 1639, 1514, 1477, 1323 and 1302 cm$^{-1}$.

Crystalline irbesartan hydrochloride sesquihydrate according to the present invention is further characterised by having a water content from about 5.7% to 7.5%.

Crystalline irbesartan hydrochloride sesquihydrate according to the present invention is further characterised as having an X-ray powder diagram, or substantially the same X-ray powder diagram, as shown in FIG. 1. Crystalline irbesartan hydrochloride sesquihydrate according to the present invention is further characterised as having characteristic peaks (2θ): 7.49, 8.24, 11.01, 14.92, 15.32, 16.28, 17.38, 22.52, 22.98, 23.42, 24.68, 26.57, 27.00 and 28.47°.

Further characterising data for crystalline irbesartan hydrochloride sesquihydrate according to the present invention as obtained by X-ray diffraction is shown in following table 1.

TABLE 1

| Peak No. | 2θ (deg) | d (A) | I/II | FWHM (deg) | Intensity (Counts) | Integrated (Counts) |
|---|---|---|---|---|---|---|
| 1 | 7.0000 | 12.61783 | 9 | 0.30340 | 119 | 2189 |
| 2 | 7.4856 | 11.80035 | 20 | 0.34170 | 280 | 5101 |
| 3 | 8.2450 | 10.71511 | 52 | 0.33340 | 722 | 13970 |
| 4 | 11.0069 | 8.03185 | 61 | 0.34710 | 846 | 17285 |
| 5 | 12.8800 | 6.86770 | 38 | 0.36720 | 519 | 8115 |
| 6 | 13.0800 | 6.76314 | 36 | 0.49080 | 499 | 8702 |
| 7 | 13.6800 | 6.46783 | 6 | 0.18460 | 79 | 871 |
| 8 | 13.9759 | 6.33155 | 29 | 0.33600 | 406 | 6511 |
| 9 | 14.9200 | 5.93296 | 65 | 0.44780 | 900 | 19460 |
| 10 | 15.3200 | 5.77894 | 67 | 0.32920 | 932 | 15317 |
| 11 | 16.2802 | 5.44020 | 33 | 0.35440 | 460 | 8936 |
| 12 | 17.3802 | 5.09829 | 50 | 0.34860 | 696 | 11627 |
| 13 | 17.8000 | 4.97898 | 21 | 0.36500 | 296 | 5445 |
| 14 | 18.2883 | 4.84713 | 11 | 0.28330 | 152 | 2161 |
| 15 | 19.0548 | 4.65384 | 15 | 0.28560 | 206 | 2893 |
| 16 | 20.0911 | 4.41607 | 24 | 0.33310 | 332 | 6756 |
| 17 | 20.5400 | 4.32056 | 12 | 0.00000 | 160 | 0 |
| 18 | 21.0682 | 4.21342 | 40 | 0.35940 | 546 | 11154 |
| 19 | 21.5400 | 4.12218 | 10 | 0.40500 | 139 | 3220 |
| 20 | 22.0800 | 4.02258 | 21 | 0.17640 | 286 | 3200 |
| 21 | 22.5200 | 3.94497 | 79 | 0.40400 | 1096 | 30030 |
| 22 | 22.9800 | 3.86703 | 57 | 0.00000 | 788 | 0 |
| 23 | 23.4200 | 3.79536 | 100 | 0.65620 | 1381 | 42435 |
| 24 | 24.0200 | 3.70190 | 9 | 0.20720 | 128 | 2678 |
| 25 | 24.6797 | 3.60442 | 24 | 0.34520 | 325 | 6592 |
| 26 | 25.9000 | 3.43729 | 11 | 0.33600 | 156 | 3086 |
| 27 | 26.5731 | 3.35173 | 50 | 0.44340 | 691 | 13760 |
| 28 | 27.0000 | 3.29970 | 29 | 0.41340 | 405 | 7929 |
| 29 | 27.5207 | 3.23844 | 15 | 0.33860 | 208 | 3561 |
| 30 | 28.0000 | 3.18409 | 5 | 0.32000 | 74 | 1574 |
| 31 | 28.4714 | 3.13243 | 35 | 0.35110 | 478 | 7632 |
| 32 | 28.9200 | 3.08485 | 15 | 0.52800 | 207 | 4757 |
| 33 | 29.4168 | 3.03387 | 17 | 0.36820 | 230 | 3931 |
| 34 | 30.1680 | 2.96002 | 9 | 0.51600 | 119 | 3108 |
| 35 | 30.8863 | 2.89280 | 11 | 0.36160 | 156 | 2887 |
| 36 | 32.1204 | 2.78441 | 28 | 0.57740 | 389 | 12206 |
| 37 | 33.4207 | 2.67899 | 12 | 0.38320 | 163 | 3701 |
| 38 | 35.0527 | 2.55791 | 15 | 0.45740 | 205 | 5737 |
| 39 | 36.9991 | 2.42769 | 6 | 0.27170 | 79 | 1083 |

Figure 4:
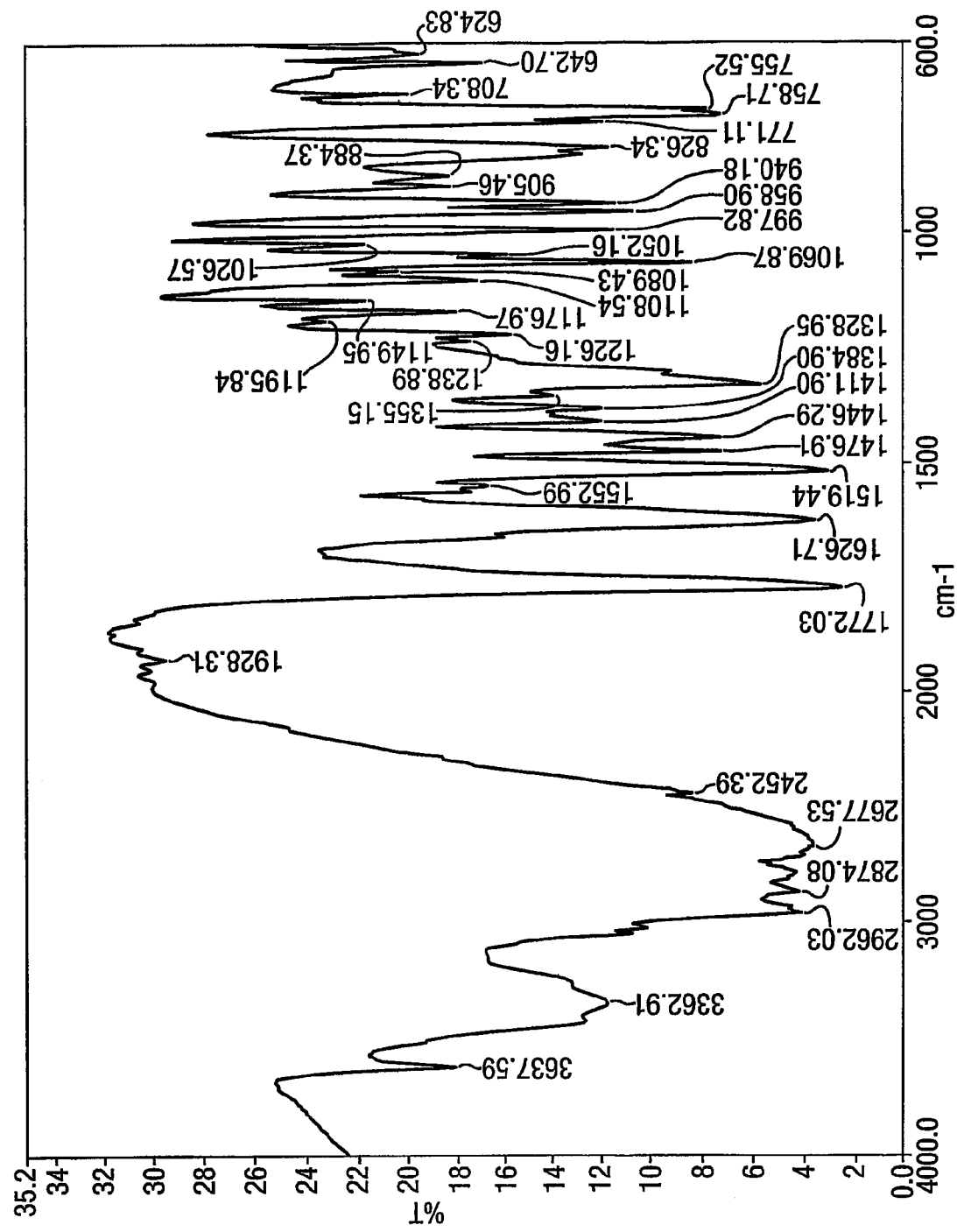
FIG. 4: An IR pattern of irbesartan hydrochloride hemihydrate obtained by using Parkin Elmer Paragon 500 Model.

There is further provided by the present invention, therefore, crystalline irbesartan hydrochloride hemihydrate having an IR pattern, or substantially the same IR pattern, as shown in FIG. 4. More particularly, irbesartan hydrochloride hemihydrate has characteristic IR absorbance at about 1772, 1627, 1519, 1476, 1226, 1070, 998, 959, 940, 708 and 645 cm$^{-1}$.

Crystalline irbesartan hydrochloride hemihydrate according to the present invention is further characterised by having a water content from about 1.7% to 2.8%, and suitably a melting point of about 186° C.

Figure 3:
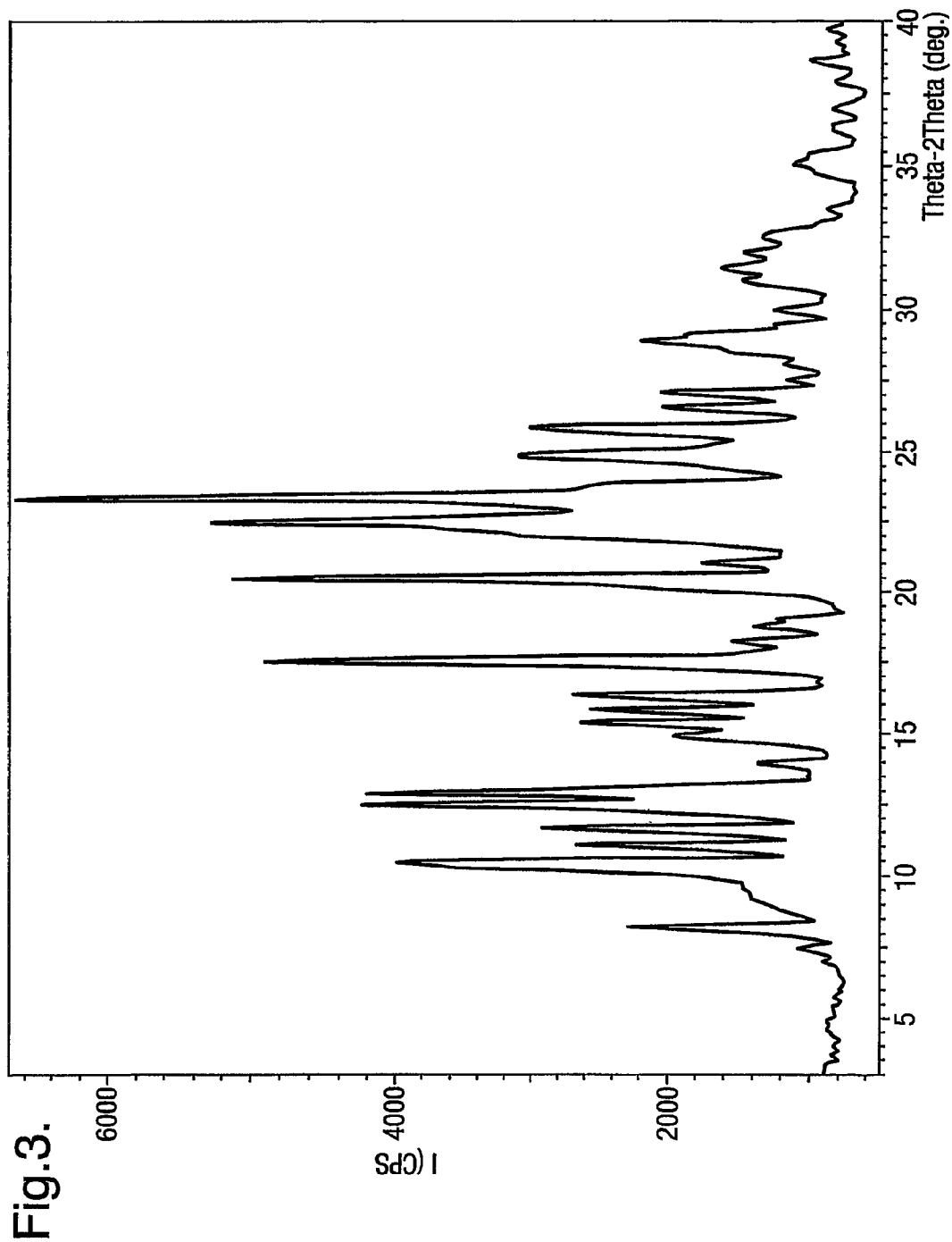
FIG. 3: An XRPD of irbesartan hydrochloride hemihydrate obtained by using a Rigaku Miniflex between 2° to 40°.

Crystalline irbesartan hydrochloride hemihydrate according to the present invention is further characterised as having an X-ray powder diagram, or substantially the same X-ray powder diagram, as shown in FIG. 3. Crystalline irbesartan hydrochloride hemihydrate according to the present invention is further characterised as having characteristic peaks (2θ): 8.2, 10.33, 11.02, 12.42, 12.87, 15.32, 15.76, 16.25, 17.46, 22.42, 22.98, 23.3, 24.81, 25.75, 26.53 and 27.06°.

Further characterising data for crystalline irbesartan hemihydrate according to the present invention as obtained by X-ray diffraction is shown in following table 2.

TABLE 2

| Peak No. | 2θ (deg) | d (A) | I/II | FWHM (deg) | Intensity (Counts) | Integrated (Counts) |
|---|---|---|---|---|---|---|
| 1 | 8.2060 | 10.76595 | 23 | 0.24610 | 348 | 4678 |
| 2 | 9.2000 | 9.60487 | 6 | 0.62760 | 86 | 2901 |
| 3 | 9.5800 | 9.22472 | 6 | 0.00000 | 93 | 0 |
| 4 | 10.3309 | 8.55584 | 51 | 0.44560 | 763 | 19058 |

TABLE 2-continued

| Peak No. | 2θ (deg) | d (A) | I/II | FWHM (deg) | Intensity (Counts) | Integrated (Counts) |
|---|---|---|---|---|---|---|
| 5 | 11.0174 | 8.02422 | 27 | 0.23210 | 401 | 4923 |
| 6 | 11.6076 | 7.61751 | 32 | 0.24750 | 481 | 6343 |
| 7 | 12.4194 | 7.12135 | 57 | 0.31450 | 850 | 14204 |
| 8 | 12.8665 | 6.87488 | 57 | 0.33300 | 849 | 13723 |
| 9 | 13.2200 | 6.69183 | 12 | 0.14580 | 186 | 2503 |
| 10 | 13.9662 | 6.33592 | 7 | 0.23240 | 112 | 1398 |
| 11 | 14.9000 | 5.94088 | 19 | 0.41400 | 286 | 5925 |
| 12 | 15.3238 | 5.77752 | 31 | 0.29240 | 467 | 6546 |
| 13 | 15.7624 | 5.61773 | 30 | 0.28160 | 447 | 6613 |
| 14 | 16.2552 | 5.44851 | 32 | 0.30500 | 482 | 7766 |
| 15 | 17.4652 | 5.07366 | 73 | 0.34960 | 1097 | 21929 |
| 16 | 18.2600 | 4.85458 | 13 | 0.27160 | 194 | 3791 |
| 17 | 18.8000 | 4.71634 | 11 | 0.29100 | 164 | 2347 |
| 18 | 19.0600 | 4.65258 | 8 | 0.23460 | 126 | 1489 |
| 19 | 20.0200 | 4.43159 | 15 | 0.14620 | 219 | 2671 |
| 20 | 20.4206 | 4.34555 | 76 | 0.28510 | 1134 | 17600 |
| 21 | 21.0003 | 4.22689 | 12 | 0.24470 | 185 | 2766 |
| 22 | 21.5800 | 4.11463 | 6 | 0.14480 | 88 | 1019 |
| 23 | 21.8800 | 4.05889 | 32 | 0.23000 | 473 | 10189 |
| 24 | 22.1400 | 4.01181 | 43 | 0.00000 | 638 | 0 |
| 25 | 22.4200 | 3.96234 | 74 | 0.46460 | 1107 | 28888 |
| 26 | 22.9800 | 3.86703 | 35 | 0.00000 | 531 | 0 |
| 27 | 23.2962 | 3.81525 | 100 | 0.30100 | 1498 | 26406 |
| 28 | 23.8200 | 3.73253 | 20 | 0.20920 | 301 | 5578 |
| 29 | 24.3600 | 3.65099 | 6 | 0.13140 | 94 | 847 |
| 30 | 24.8143 | 3.58517 | 33 | 0.45850 | 501 | 12503 |
| 31 | 25.2400 | 3.52566 | 9 | 0.00000 | 136 | 0 |
| 32 | 25.7510 | 3.45684 | 34 | 0.38890 | 503 | 10874 |
| 33 | 26.5309 | 3.35697 | 17 | 0.25470 | 259 | 3517 |
| 34 | 27.0573 | 3.29284 | 18 | 0.25690 | 275 | 4108 |
| 35 | 28.5000 | 3.12935 | 11 | 0.24000 | 166 | 2819 |
| 36 | 28.8600 | 3.09113 | 22 | 0.43560 | 334 | 4972 |
| 37 | 29.1200 | 3.06412 | 17 | 0.26460 | 251 | 2907 |
| 38 | 29.4800 | 3.02751 | 5 | 0.16220 | 78 | 929 |
| 39 | 29.9653 | 2.97958 | 6 | 0.24530 | 87 | 1111 |

Figure 6:
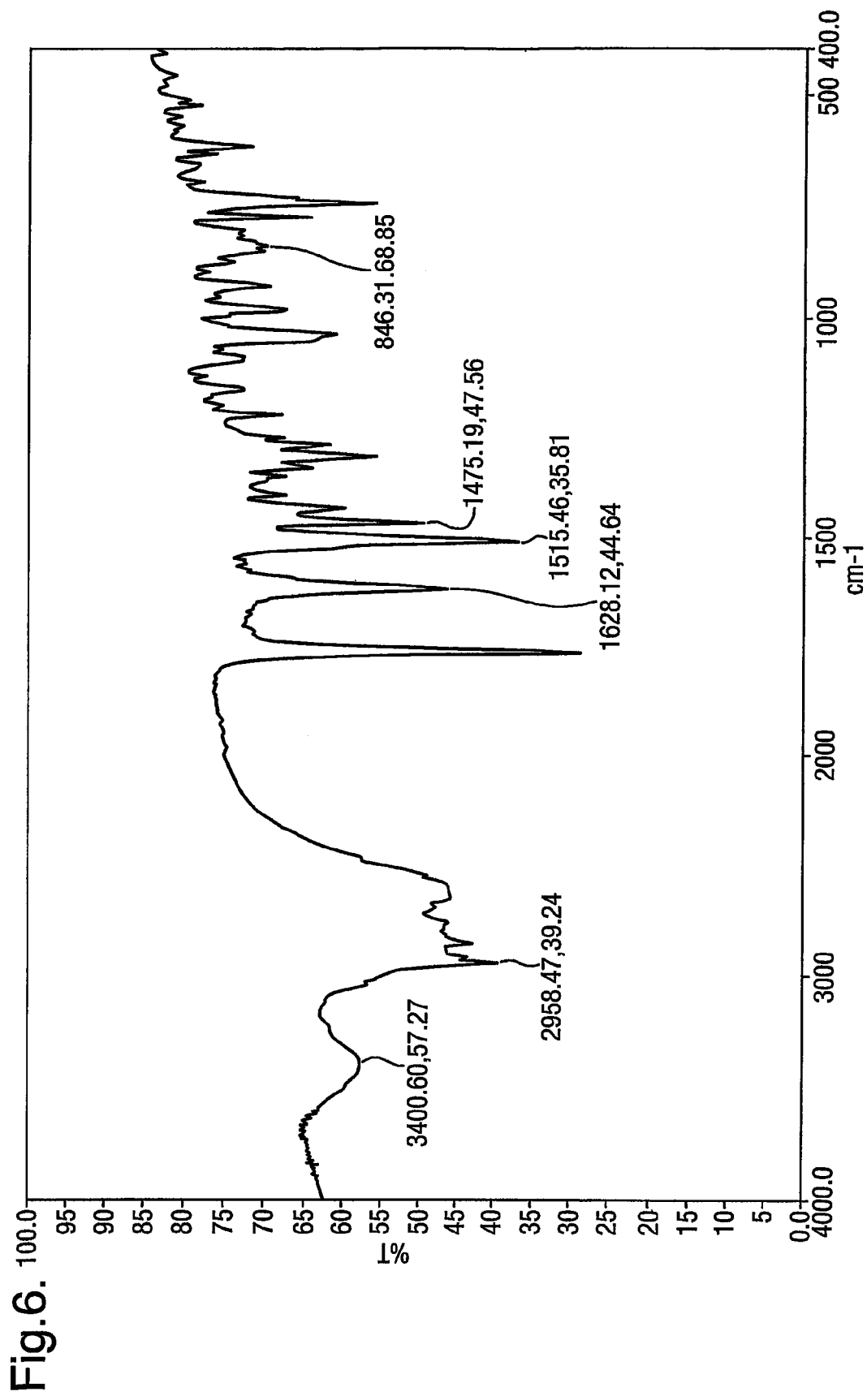
FIG. 6: An IR pattern of anhydrous irbesartan hydrochloride obtained by using a Parkin Elmer Paragon 500 Model.

There is further provided by the present invention crystalline anhydrous irbesartan hydrochloride having an IR pattern, or substantially the same IR pattern, as shown in FIG. 6. More particularly, anhydrous irbesartan hydrochloride has characteristic IR absorbance at about 3400, 2958, 1628, 1515, 1475, and 846 cm$^{-1}$.

Crystalline anhydrous irbesartan according to the present invention is further characterised by having a water content from about 0.2 to 0.9%.

Figure 5:
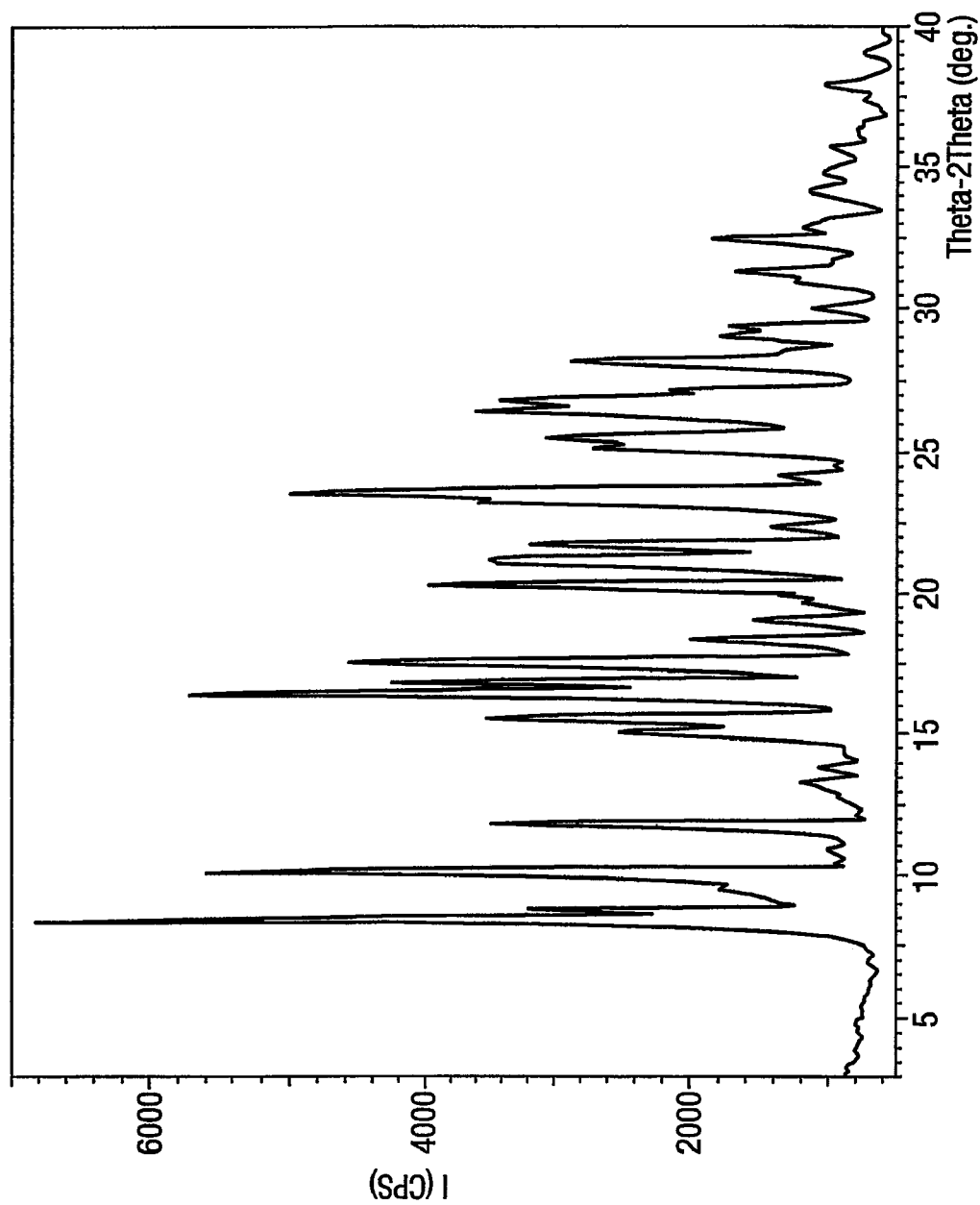
FIG. 5: An XRPD of anhydrous irbesartan hydrochloride according to the present invention obtained by using a Rigaku Miniflex between 2° to 40°.

Crystalline anhydrous irbesartan hydrochloride according to the present invention is further characterised as having an X-ray powder diagram, or substantially the same X-ray powder diagram, as shown in FIG. 5. Crystalline anhydrous irbesartan hydrochloride according to the present invention is further characterised as having characteristic peaks (2θ): 8.0, 8.35, 8.70, 9.48, 10.05, 11.76, 15.00, 15.48, 16.38, 16.79, 17.47, 20.26, 21.12, 23.54, 25.14, 26.44, 26.78, 28.12, and 32.45°.

Further characterising data for crystalline anhydrous irbesartan hydrochloride according to the present invention as obtained by X-ray diffraction is shown in following table 3.

TABLE 3

| Peak No. | 2θ (deg) | d (A) | I/II | FWHM (deg) | Intensity (Counts) | Integrated (Counts) |
|---|---|---|---|---|---|---|
| 1 | 8.0000 | 11.04270 | 12 | 0.18660 | 192 | 3184 |
| 2 | 8.3519 | 10.57820 | 100 | 0.27240 | 1614 | 21537 |
| 3 | 8.7000 | 10.15572 | 39 | 0.26320 | 630 | 10111 |
| 4 | 9.1000 | 9.71019 | 8 | 0.00000 | 134 | 0 |
| 5 | 9.4800 | 9.332180 | 15 | 0.00000 | 246 | 0 |
| 6 | 10.0523 | 8.79234 | 79 | 0.29900 | 1270 | 23649 |
| 7 | 11.7572 | 7.52092 | 45 | 0.26360 | 719 | 10737 |
| 8 | 13.2750 | 6.66423 | 7 | 0.39000 | 118 | 3856 |
| 9 | 15.0000 | 5.90150 | 28 | 0.33340 | 446 | 8600 |
| 10 | 15.4862 | 5.71729 | 44 | 0.33170 | 710 | 12135 |
| 11 | 16.3854 | 5.40551 | 81 | 0.31500 | 1306 | 21489 |
| 12 | 16.7950 | 5.27459 | 57 | 0.26290 | 921 | 12247 |
| 13 | 17.4706 | 5.07211 | 62 | 0.36070 | 1006 | 19518 |
| 14 | 18.2997 | 4.84413 | 21 | 0.28850 | 333 | 5096 |
| 15 | 19.0343 | 4.65881 | 13 | 0.28680 | 203 | 3007 |
| 16 | 19.7200 | 4.49833 | 5 | 0.25600 | 81 | 1377 |
| 17 | 20.2626 | 4.37908 | 51 | 0.27480 | 827 | 11941 |
| 18 | 21.1227 | 4.20267 | 41 | 0.47520 | 664 | 16494 |
| 19 | 21.7009 | 4.09198 | 36 | 0.30140 | 574 | 8490 |
| 20 | 22.3465 | 3.97520 | 6 | 0.22450 | 97 | 1101 |
| 21 | 23.2200 | 3.82760 | 43 | 0.32700 | 690 | 11466 |
| 22 | 23.5400 | 3.77629 | 67 | 0.36460 | 1083 | 17624 |
| 23 | 24.1758 | 3.67839 | 7 | 0.23170 | 109 | 1362 |
| 24 | 25.1400 | 3.53946 | 29 | 0.33900 | 464 | 7612 |
| 25 | 25.5200 | 3.48761 | 34 | 0.38540 | 553 | 10609 |
| 26 | 26.1200 | 3.40884 | 16 | 0.24940 | 256 | 3524 |
| 27 | 26.4400 | 3.36830 | 45 | 0.40880 | 719 | 10846 |
| 28 | 26.7800 | 3.32631 | 42 | 0.39220 | 675 | 10378 |
| 29 | 27.1400 | 3.28300 | 22 | 0.27200 | 354 | 4680 |
| 30 | 28.1193 | 3.17085 | 34 | 0.35870 | 553 | 9910 |
| 31 | 28.5400 | 3.12506 | 9 | 0.29600 | 153 | 2817 |
| 32 | 29.0200 | 3.07445 | 18 | 0.26400 | 285 | 3927 |
| 33 | 29.3600 | 3.03961 | 17 | 0.24820 | 275 | 3768 |
| 34 | 30.0492 | 2.97145 | 7 | 0.27350 | 120 | 1817 |
| 35 | 30.9800 | 2.88426 | 9 | 0.28660 | 148 | 2179 |
| 36 | 31.3038 | 2.85516 | 16 | 0.38770 | 265 | 5328 |
| 37 | 32.1800 | 2.77939 | 6 | 0.19120 | 96 | 1267 |
| 38 | 32.4548 | 2.75648 | 20 | 0.30330 | 320 | 5504 |
| 39 | 32.8600 | 2.72341 | 9 | 0.00000 | 144 | 0 |

Figure 7:
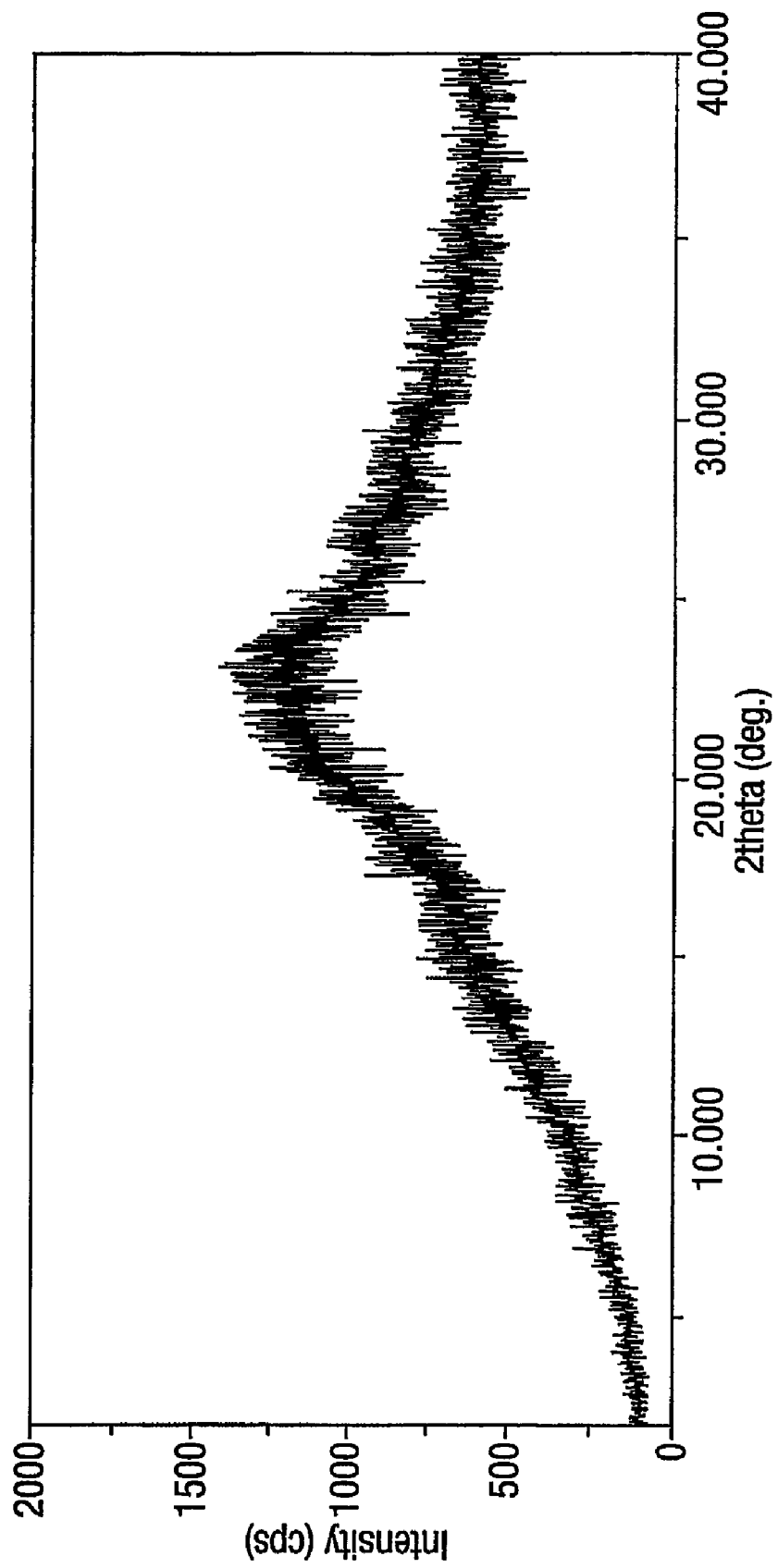
FIG. 7: An XRPD of amorphous irbesartan hydrochloride according to the present invention obtained by using a Rigaku Miniflex between 2° to 40°.
Figure 8:
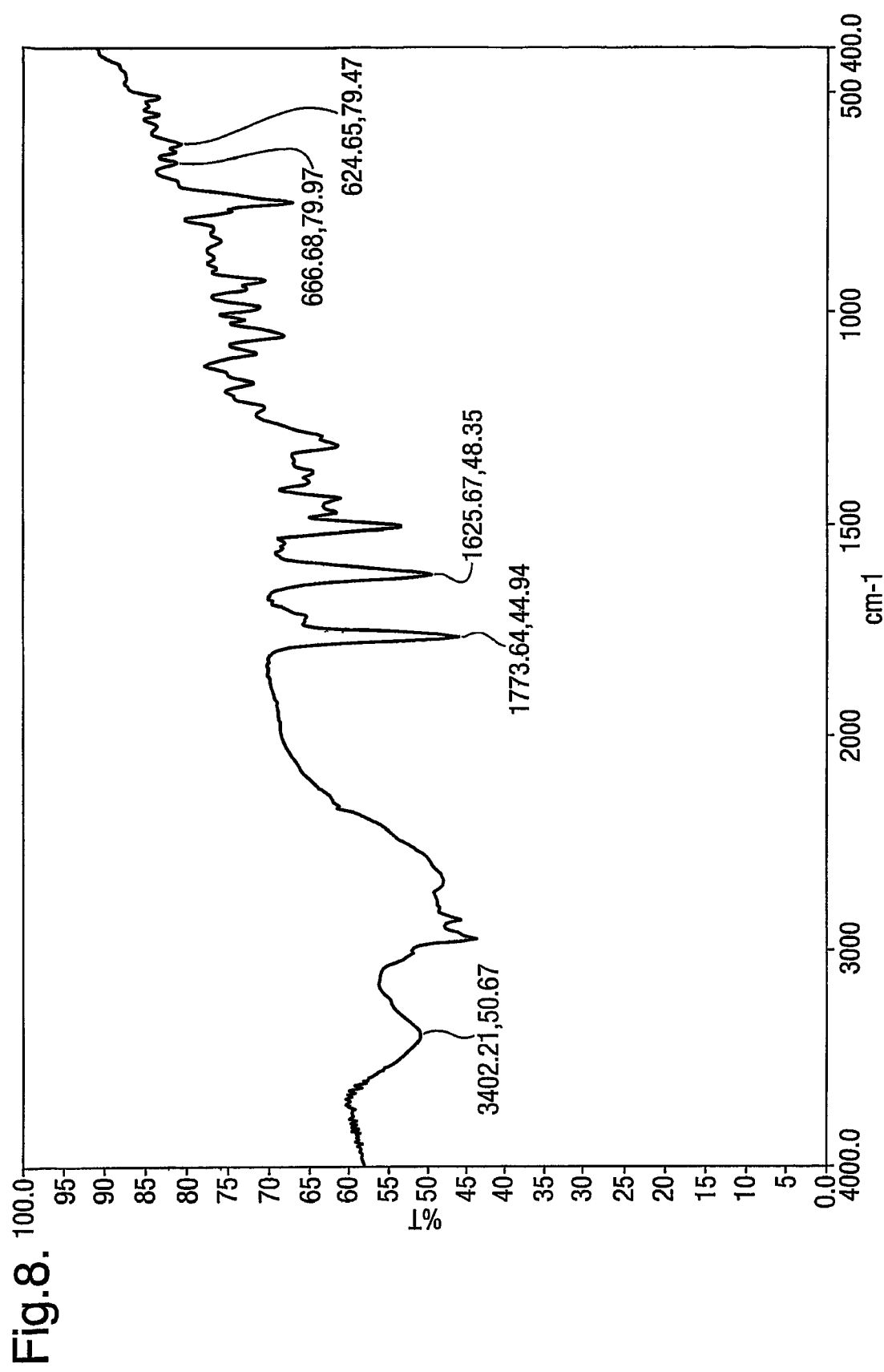
FIG. 8: An IR pattern of amorphous irbesartan hydrochloride obtained by using a Parkin Elmer Paragon 500 Model.

The present invention further provides amorphous irbesartan hydrochloride. Amorphous irbesartan hydrochloride as provided by the present invention can be characterised by an IR pattern, or substantially the same IR pattern, as shown in FIG. 8. More particularly, amorphous irbesartan hydrochloride has characteristic IR absorbance at about 3402, 1773, 1625, 666 and 624 cm$^{-1}$. Amorphous irbesartan hydrochloride according to the present invention is further characterised as having an X-ray powder diagram, or substantially the same X-ray powder diagram, as shown in FIG. 7.

Irbesartan hydrochloride, preferably irbesartan hydrochloride sesquihydrate according to the present invention, can be isolated directly from the final reaction mixture obtained as described above with reference to a process according to the present invention. More specifically, it is preferred that irbesartan hydrochloride, as the sesquihydrate, can be isolated directly from the final reaction mixture obtained further to detritylation of a compound of formula (IV).

Irbesartan hydrochloride hemihydrate according to the present invention can be prepared by drying the sesquihydrate at higher temperatures, or by dissolving the sesquihydrate in a solvent, such as methanol, at elevated temperatures and concentrating to a residue and subsequent precipitating with a non-solvent, such as ethyl acetate. Alternatively, the hemihydrate may be prepared from amorphous irbesartan free base (known in the art, for example WO 03/050110) by dissolving the amorphous form in a solvent mixture of methanol and water at elevated temperatures and concentrating to a residue and subsequent precipitation with a non-solvent, such as ethyl acetate.

Anhydrous irbesartan hydrochloride according to the present invention can be prepared by repeatedly stirring the sesquihydrate in a solvent, such as methanol, or a methanol-ethylacetate mixture at elevated temperatures and subsequently precipitating with a non-solvent, such as ethyl acetate. Alternatively, the anhydrous form may be prepared from irbesartan in sesquihydrate form or hemihydrate form, by drying the product at elevated temperature (80-85° C.).

Amorphous irbesartan hydrochloride may be prepared from irbesartan in sesquihydrate form, hemihydrate form or anhydrous form by drying the product at elevated temperature (90-105° C.).

Irbesartan as provided by the present invention is an angiotensin II antagonist and is thus useful in the treatment of various cardiovascular complaints, especially hypertension, heart failure and venous insufficiency, as well as in the treatment of glaucoma, diabetic retinopathy and various complaints of the central nervous system, for example anxiety, depression, memory deficiencies or Alzheimer's disease.

The present invention further provides, therefore, a pharmaceutical composition comprising a therapeutically effective dose of irbesartan according to the invention, together with a pharmaceutically acceptable carrier, diluent or excipient therefor. Excipients are chosen according to the pharmaceutical form and the desired mode of administration.

In the pharmaceutical compositions of the present invention for oral, sublingual, subcutaneous, intramuscular, intravenous, topical, intratracheal, intranasal, transdermal or rectal administration, irbesartan according to the present invention is administered to animals and humans in unit forms of administration, mixed with conventional pharmaceutical carriers, for the prophylaxis or treatment of the above disorders or diseases. The appropriate unit forms of administration include forms for oral administration, such as tablets, gelatin capsules, powders, granules and solutions or suspensions to be taken orally, forms for sublingual, buccal, intratracheal or intranasal administration, forms for subcutaneous, intramuscular or intravenous administration and forms for rectal administration. For topical application, irbesartan according to the present invention can be used in creams, ointments or lotions.

To achieve the desired prophylactic or therapeutic effect, the dose of irbesartan according to the present invention can vary between 0.01 and 50 mg per kg of body weight per day. Each unit dose can contain from 0.1 to 1000 mg, preferably 1 to 500 mg, of irbesartan according to the present invention in combination with a pharmaceutical carrier. This unit dose can be administered 1 to 5 times a day so as to administer a daily dosage of 0.5 to 5000 mg, preferably 1 to 2500 mg.

When a solid composition in the form of tablets is prepared, irbesartan according to the present invention is mixed with a pharmaceutical vehicle such as gelatin, starch, lactose, magnesium stearate, talc, gum arabic or the like. The tablets can be coated with sucrose, a cellulose derivative or other appropriate substances, or else they can be treated so as to have a prolonged or delayed activity and so as to release a predetermined amount of active principle continuously.

A preparation in the form of gelatin capsules can be obtained by mixing irbesartan according to the present invention with a diluent and pouring the resulting mixture into soft or hard gelatin capsules.

A preparation in the form of a syrup or elixir or for administration in the form of drops can contain irbesartan according to the present invention in conjunction with a sweetener, which is preferably calorie-free, methylparaben and propylparaben as antiseptics, as well as a flavoring and an appropriate color.

Water-dispersible granules or powders can contain irbesartan according to the present invention mixed with dispersants or wetting agents, or suspending agents such as polyvinylpyrrolidone, as well as with sweeteners or taste correctors.

Rectal administration is effected using suppositories prepared with binders which melt at the rectal temperature, for example polyethylene glycols.

Parenteral administration is effected using aqueous suspensions, isotonic saline solutions or sterile and injectable solutions which contain pharmacologically compatible dispersants and/or wetting agents, for example propylene glycol or butylene glycol.

Irbesartan according to the present invention can also be formulated as microcapsules, with one or more carriers or additives if appropriate.

There is also provided by the present invention irbesartan substantially as hereinbefore described for use in therapy.

The present invention further provides irbesartan substantially as hereinbefore described, for use in the manufacture of a medicament for the treatment of a disease state prevented, ameliorated or eliminated by the administration of an angiotensin II antagonist as described herein.

The present invention also provides a method of treating a disease state prevented, ameliorated or eliminated by the administration of an angiotensin II antagonist in a patient in need of such treatment, which method comprises administering to the patient a therapeutically effective amount of irbesartan substantially as hereinbefore described.

The present invention can be further illustrated by the following Figures and non-limiting Examples.

EXAMPLES

Example 1

32.8 g of powdered sodium hydroxide was added to the mixture of 5-(4'-bromo methyl biphenyl-2-yl)-1-trityl-1H-tetrazole (119 g) and 2n-butyl-1,3-diazaspiro (4,4) non-1-en-4-one HCl (50 g) in toluene (500 ml) in the presence of tetra butyl ammonium bromide (4.3 g). The mixture was heated to about 85° C. for about 2 hours. After reaction completion, the reaction mass was cooled to about 25° C., washed with purified water (200 ml×2). The toluene layer was separated. To this 4N HCl was added (600 ml). The contents were heated to about 55° C. for about 45 minutes. After reaction completion, the product was isolated by filtration at 25-30° C. The wet cake was dried at about 60° C. under vacuum to obtain 87.5 g (94%) of the product characterised as irbesartan hydrochloride sesquihydrate by moisture content and powder x-ray diffraction.

Example 2

32.8 g of sodium hydroxide was dissolved in 480 ml of purified water and added to the mixture of 5-(4'-bromomethyl biphenyl-2-yl)-1-trityl-1H-tetrazole (119 g) and 2n-butyl-1,3-diazaspiro-(4,4)-non-1-en-4-one HCl (50 g) in toluene (500 ml) in the presence of tetra butyl ammonium bromide (4.3 g). The mixture was heated to about 85° C. for about 2 hours. After reaction completion, the reaction mass was cooled to about 25° C. and the toluene layer separated. The toluene layer was washed with water (200 ml×2). The toluene layer was again separated. To this 4N HCl was added (600 ml). The contents were then heated to about 55° C. for about 45 minutes. After reaction completion, the product was isolated by filtration at 25-30° C. The wet cake was dried at about 60° C. under vacuum to obtain 84.5 g (91%) of the product characterised as irbesartan hydrochloride sesquihydrate by moisture content and powder x-ray diffraction.

Example 3

32.8 g of powdered sodium hydroxide was added to the mixture of 5-(4'-bromomethyl biphenyl-2-yl)-1-trityl-1H-tetrazole (119 g) and 2n-butyl-1,3-diazaspiro (4,4)-non-1-en-4 one HCl (50 g) in toluene (500 ml). The mixture was heated to about 85° C. for about 2 to 4 hours.

After reaction completion, the reaction mass was cooled to about 25° C., washed with purified water (200 ml×2). The toluene layer was separated and 4N HCl was added (600 ml). The contents were heated to about 55° C. for about 75 minutes. After reaction completion, the product was isolated by filtration at about 25-30° C. The wet cake was dried at about 60° C. under vacuum to obtain 60.5 g (65%) of the product characterised as irbesartan hydrochloride sesquihydrate.

Example 4

42.6 g of powdered potassium hydroxide was added to the mixture of 5-(4'-bromomethyl biphenyl-2-yl)-1-trityl-1H-tetrazole (119 g) and 2n-butyl-1,3-diazaspiro (4,4)-non-1-en-4-one HCl (50 g) in toluene (500 ml). The mixture was heated to about 85° C. for about 2 hours.

After reaction completion, the reaction mass was cooled to about 25° C., washed with purified water (200 ml×2). The toluene layer was separated. To this, 4N HCl was added (600 ml). The contents were heated to about 55° C. for about 45 minutes. After reaction completion, the product was isolated by filtration at 25-30° C. and dried under vacuum at 80° C. to give 62.5 g (69%) of irbesartan hydrochloride hemihydrate.

Example 5

32.8 g of sodium hydroxide dissolved in 480 ml of purified water was added to the mixture of 5-(4'-bromomethyl biphenyl-2-yl)-1-trityl-1H-tetrazole (119 g) and 2n-butyl-1,3-diazaspiro (4,4) non-1-en-4 one HCl (50 g) and tetra butyl ammonium bromide (4.3 g) in toluene (500 ml). The mixture was heated to about 85° C. for about 2 hours. After reaction completion, the reaction mass was cooled to about 25° C. and the toluene layer separated. The toluene layer was washed with water (200 ml×2). The toluene layer was again separated. To this, 4N HCl was added (600 ml). The contents were then heated to about 55° C. for about 45 minutes. After reaction completion, the product was isolated by filtration at 25-30° C. The wet cake was dried at about 80° C. under vacuum to obtain 85.5 g (92%) of the product characterised as irbesartan hydrochloride hemihydrate.

Example 5A

Example 5 was repeated but with an added isolation step before the detritylation, so as to illustrate the difference between a one-pot process of the present invention (Example 5), and a non-one-pot process of the prior art (this Example).

16.4 g of sodium hydroxide dissolved in 240 ml of purified water was added to the mixture of 5-(4'-bromomethyl-biphenyl-2-yl)-1-trityl-1H-tetrazole (59.5 g) and 2n-butyl-1,3-diazaspiro (4,4) non-1-en-4-one HCl (25 g) and tetra butyl ammonium bromide (2.15 g) in toluene (250 ml). The mixture was heated to about 85° C. for about 2 hours. After reaction completion, the reaction mass was cooled to about 25° C. and the toluene layer separated. The aqueous phase was extracted with toluene (105 ml). The combined organic layer was evaporated. The residue was dissolved in acetone (208 ml) and 3N HCl was added (600 ml). The contents were stirred at room temperature until reaction completion (as monitored by TLC). After reaction completion, a solution of KOH (30.4 g) in water (208 ml) was slowly added and acetone was evaporated under reduced pressure. The precipitated trityl alcohol was filtered and washed with water (2×10$^5$ ml). The filtrate was washed with toluene and slowly acidified to pH 4 with 3 N HCl. The suspension was cooled to 0-4° C., stirred for an additional 30 minutes and filtered. The cake was washed with cold isopropanol (2×50 ml) and dried under reduced pressure at 50-60° C. to yield irbesartan free base (92.0%).

Example 6

42.6 g of potassium hydroxide was dissolved in 480 ml of purified water which was added to a mixture of 5-(4'-bromo methyl biphenyl-2-yl)-1-trityl-1H-tetrazole (119 g) and 2n-butyl-1,3-diazaspiro (4,4) non-1-en-4-one HCl (50 g) and tetra butyl ammonium bromide (4.3 g) in toluene (500 ml). The mixture was heated to about 85° C. for about 2 hours. After reaction completion, the reaction mass was cooled to about 25° C. and the toluene layer separated. The toluene layer was washed with water (200 ml×2). The toluene layer was again separated. To this 4N HCl was added (600 ml). The contents were then heated to about 55° C. for about 45 minutes. After reaction completion, the product was isolated by direct filtration at 25-30° C. The wet cake was dried at about 60° C. under vacuum to obtain 87.5 g (94%) of the product characterised as irbesartan hydrochloride sesquihydrate.

Example 7

About 32.8 g of powdered sodium hydroxide was added to the mixture of 5-(4'-bromo methyl biphenyl-2-yl)-1-trityl-1H-tetrazole (119 g) and 2n-butyl-1,3-diazaspiro (4,4) non-1-en-4-one HCl (50 g) in xylene (500 ml) in the presence of 18-Crown-6 (4.0 g). The mixture was heated to about 85° C. for about 2 to 4 hours. After reaction completion, the reaction mass was cooled to about 25° C., the xylene layer was washed with purified water (200 ml×2) and then separated. To this 4N HCl was added (600 ml). The contents were heated to about 55° C. for about 45 minutes. After reaction completion, the product was isolated by direct filtration at 25-30° C. The wet cake was dried at about 60° C. under vacuum to obtain 87.5 g (94%) of the product characterised as irbesartan hydrochloride sesquihydrate.

Example 8

42.6 g of powdered potassium hydroxide was added to the mixture of 5-(4'-bromo methyl biphenyl-2-yl)-1-trityl-1H-tetrazole (119 g) and 2n-butyl-1,3-diazaspiro (4,4) non-1-en-4 one HCl (50 g) in xylene (500 ml) along with tetra butyl ammonium bromide (4.3 g). The mixture was heated to about 85° C. for about 2 hours. After reaction completion, the reaction mass was cooled to about 25° C. and the xylene layer was washed with water (200 ml×2).

The xylene layer was separated. To this 4N HCl was added (600 ml). The contents were then heated to about 55° C. for about 45 minutes. After reaction completion, the product was isolated by filtration at 25-30° C. The wet cake was dried at about 60° C. under vacuum to obtain 87.5 g (94%) of the product characterised as irbesartan hydrochloride sesquihydrate.

Example 9

32.8 g of potassium carbonate was added to the mixture of 5-(4'-bromo methyl biphenyl-2-yl)-1-trityl-1H-tetrazole (119 g) and 2n-butyl-1,3-diazaspiro (4,4) non-1-en-4 one HCl (50 g) in acetonitrile (500 ml). The contents were heated to about 70° C. to obtain a condensed product. The product was isolated upon filtration, with the product being in the filtrate. The filtrate was distilled under reduced pressure to a residue. To this mixture 4N HCl (400 ml) and toluene (400 ml) were added, heated to about 55° C., maintained for 1 hour and filtered at room temperature. The wet cake was dried at about 60° C. under vacuum to obtain 80 g (85%) of the product characterised as irbesartan hydrochloride sesquihydrate.

Example 10

109.3 g of potassium carbonate was added to the mixture of 5-(4'-bromo methyl biphenyl-2-yl)-1-trityl-1H-tetrazole (119 g) and 2n-butyl-1,3-diazaspiro (4,4) non-1-en-4 one HCl (50 g) and tetra butyl ammonium bromide (4.3 g) in MIBK (500 ml). The mixture was heated to about 85° C. for about 2 hours. After reaction completion, the reaction mass was cooled to about 25° C., washed with purified water (200 ml×2). The MIBK layer was separated. To this 4N HCl was added (600 ml). The contents were heated to about 55° C. for about 45 minutes. After reaction completion, the product was isolated by filtration at 25-30° C. The wet cake was dried at about 60° C. under vacuum to obtain 75 g (80%) of the product characterised as irbesartan hydrochloride sesquihydrate.

Example 11

109.3 g of potassium carbonate dissolved in 480 ml of purified water was added to the mixture of 5-(4'-bromo methyl biphenyl-2-yl)-1-trityl-1H-tetrazole (119 g) and 2n-butyl-1,3-diazaspiro (4,4) non-1-en-4 one HCl (50 g) in MIBK (500 ml). The mixture was heated to about 85° C. for about 2 hours. After reaction completion, the reaction mass was cooled to about 25° C. and the MIBK layer separated. The MIBK layer was washed with water (200 ml×2). The MIBK layer was again separated. To this, 4N HCl was added (600 ml). The contents were then heated to about 55° C. for about 45 minutes. After reaction completion, the product was isolated by filtration at 25-30° C. The wet cake was dried at about 80° C. under vacuum to obtain 62.5 g (69%) of the product characterised as irbesartan hydrochloride hemihydrate.

Example 12

109.3 g of potassium carbonate was added to the mixture of 5-(4'-bromo methyl biphenyl-2-yl)-1-trityl-1H tetrazole (119 g) and 2n-butyl-1,3-diazaspiro (4,4)non-1-en-4 one HCl (50 g) in DMF (250 ml). The contents were heated to about 85° C. The inorganics were filtered off. The filtrate was distilled under reduced pressure to residue. To this mixture aq. HCl and toluene were added, heated to about 55° C. and filtered at room temperature. The wet cake was dried at about 60° C. under vacuum to obtain 80 g (86%) of the product characterised as irbesartan hydrochloride sesquihydrate.

Example 13

44.28 g of sodium methoxide was added to a mixture of 5-(4'-bromomethyl biphenyl-2-yl)-1-trityl-1H tetrazole (119 g) and 2n-butyl-1,3-diazaspiro (4,4) non-1-en-4-one HCl in DMF (250 ml). The contents were heated to about 85° C. The product was isolated upon filtration of inorganics, with the product being in the filtrate. The filtrate was distilled under reduced pressure to residue. To this a mixture of hydrochloric acid and toluene was added and heated to about 55° C. for 1 hour and filtered at room temperature, dried under vacuum at 60° C. to yield irbesartan hydrochloride sesquihydrate 80 g (86%).

Example 14

About 52.0 g of sodium t-butoxide was added to the mixture of 5-(4'-bromo methyl biphenyl-2-yl)-1-trityl-1H-tetrazole (119 g) and 2n-butyl-1,3-diazaspiro (4,4) non-1-en-4-one HCl (50 g) in toluene (500 ml) in the presence of tetra butyl ammonium bromide (4.3 g). The mixture was stirred at about 25° C. (20-30° C.) for about 4 hours. After reaction completion, the reaction mass was washed with purified water (200 ml×2). The toluene layer was separated. To this 4N HCl was added (600 ml). The contents were heated to about 55° C. for about 45 minutes. After reaction completion, the product was isolated by filtration at 25-30° C. The wet cake was dried at about 60° C. under vacuum to obtain 80.5 g (86%) of the product characterised as irbesartan hydrochloride sesquihydrate by moisture content and powder x-ray diffraction.

Example 15

About 61.0 g of potassium t-butoxide was added to the mixture of 5-(4'-bromo methyl biphenyl-2-yl)-1-trityl-1H-tetrazole (119 g) and 2n-butyl-1,3-diazaspiro (4,4) non-1-en-4-one HCl (50 g) in toluene (500 ml) in the presence of tetra butyl ammonium bromide (4.3 g). The mixture was stirred at about 25° C. (20-30° C.) for about 4 hours. After reaction completion, the reaction mass was cooled to about 25° C., washed with purified water (200 ml×2). The toluene layer was separated. To this 4N HCl was added (600 ml). The contents were heated to about 55° C. for about 45 minutes. After reaction completion, the product was isolated by filtration at 25-30° C. The wet cake was dried at about 60° C. under vacuum to obtain 85.5 g (91%) of the product characterised as irbesartan hydrochloride sesquihydrate by moisture content and powder x-ray diffraction.

Example 16

183.0 g of sodium methoxide powder was added to a mixture of 2n-butyl-1,3-diazaspiro (4,4)-non-1-en-4-one hydrochloride (100 g), 5(4'-bromomethyl biphenyl-2yl)-1-trityl 1H tetrazole (234 g) and tetra butyl ammonium bromide (10 g) in Toluene (2.4 L). The contents were heated to 80-90 C for 2 hours. After reaction completion, the reaction mass was cooled to 25-30° C., washed with water (1.0 L×3) to remove the excess alkalinity. Then to the toluene layer 4N HCl (1.2 L) was added and the contents heated to about 50° C. for about 2 hours. After reaction completion, the reaction mass was cooled to 25-30° C., product filtered and washed with water, dried under vacuum at 60° C. to yield irbesartan hydrochloride sesquihydrate 140 g (76%).

Example 17

Trityl irbesartan (25 g) was dissolved in 250 ml of toluene and 4N HCl (125 ml) was added and the contents heated to about 55° C. and maintained for about 1 hour. After reaction completion, the reaction mass was cooled to about 25° C. and filtered. The product was dried at about 60° C. under vacuum to get 15 g irbesartan hydrochloride sesquihydrate (95%).

Example 18

100 g of irbesartan hydrochloride obtained by any of the Examples 1 to 17 was dissolved in a mixture of ethyl acetate (350 ml) and methanol (150 ml). The mixture was distilled to 200 ml. To this, 200 ml of ethyl acetate was added to isolate pure irbesartan hydrochloride. The product was dried at about 100° C. under vacuum to get 94 g of the amorphous irbesartan hydrochloride having purity by HPLC greater than 99.5%.

Example 19

100 g of irbesartan hydrochloride obtained by any of Examples 1 to 17 was stirred in a mixture of 360 ml ethyl acetate, 40 ml methanol and 25 ml purified water at about 45° C., cooled to 25° C. and filtered. The product was dried at about 60° C. under vacuum to get 95 g of irbesartan hydrochloride sesquihydrate having a purity by HPLC greater than 99.5%.

Example 20

100 g of irbesartan hydrochloride obtained by any of Examples 1 to 17 was stirred in a mixture of 360 ml ethyl acetate and 40 ml methanol at about 65° C., cooled to 25° C. and filtered. The product was re-purified by repeating the same process and was dried at about 60° C. under vacuum to get 96 g of anhydrous irbesartan hydrochloride having a purity by HPLC greater than 99.5%.

Example 21

100 g of irbesartan hydrochloride obtained by any of Examples 1 to 17 was dissolved in methanol (250 ml). The mixture was distilled to residue. To this, 200 ml of ethyl acetate was added to isolate pure irbesartan hydrochloride. The product was dried at about 80° C. under vacuum to get 94 g of irbesartan hydrochloride hemihydrate having a purity by HPLC greater than 99.5%.

Example 22

100 g of irbesartan hydrochloride sesquihydrate was taken in a mixture of 250 ml toluene and 250 ml water. The pH of the reaction mass was adjusted to 6.5 to 7.0 with aqueous ammonia at 25-30° C. and stirred for about 30 minutes and filtered. The product was dried at 60° C. under vacuum to yield Form A of irbesartan free base.

Example 23

100 g of irbesartan hydrochloride hemihydrate was taken in a mixture of 250 ml toluene and 250 ml water. The pH of the reaction mass was adjusted to 6.5 to 7.0 with aqueous ammonia at 25-30° C. and stirred for about 30 minutes and filtered. The product was dried at 60° C. under vacuum to yield Form A of irbesartan free base.

Example 24

100 g of anhydrous irbesartan hydrochloride was taken in a mixture of 250 ml toluene and 250 ml water. The pH of the reaction mass was adjusted to 6.5 to 7.0 with aqueous ammonia at 25-30° C. and stirred for about 30 minutes and filtered. The product was dried at 60° C. under vacuum to yield Form A of irbesartan free base.

Example 25

100 g of irbesartan free base (Form A) was taken in a mixture of 500 ml toluene and 500 ml 4N hydrochloric acid and heated to about 100° C. for about 2 hours, cooled to 25-30 C and filtered. The product was dried at 60° C. under vacuum to yield irbesartan hydrochloride sesquihydrate.

Example 26

Example 1 of WO2004/007482

5-(4'-bromomethyl-biphenyl-2-yl)-1-trityl-1H-tetrazole (24.6 g) was charged to toluene (240 ml). To this, a solution of KOH (10.4 g), 2n-butyl-1,3-diazaspiro (4,4) non-1-en-4 one HCl (12.0 g) and $Bu_4NHSO_4$ (1.8 g) in water (40 ml) was added. The two-phase mixture was then heated to 90° C. for 90 minutes under vigorous stirring. The reaction mixture was cooled to room temperature. The toluene layer was separated and the aqueous phase was extracted with toluene (50 ml). The combined organic layer was evaporated. The residue was dissolved in acetone (100 ml) and 3N HCl (52 ml) and stirred at room temperature (TLC monitoring). A solution of KOH (14.6 g) in water (100 ml) was slowly added and acetone was evaporated under reduced pressure. The precipitated trityl alcohol was filtered and washed with water (2×50 ml). The filtrate was washed with toluene and slowly acidified to pH 4.0 with 3 N HCl. The suspension was cooled to 0-4° C., stirred for an additional 30 minutes and filtered. The cake was washed with cold isopropanol (2×25 ml) and dried under reduced pressure at 50-60° C. to yield irbesartan free base (84%).

HPLC Analysis

The products of Examples 5, 5A and 26 were analysed using HPLC. The parameters for the HPLC analysis were as follows:

Injection volume: 20 microliters
Channel: UV—VIS_1Run time: 45 minutes
Wavelength: 237 nm The results for the products of the three examples are as follows.

TABLE 4

HPLC of product of Example 5 process

| No. | Peak Name | Ret. Time min | Area mAU*min | Rel. Area % |
|---|---|---|---|---|
| 1 | n.a. | 5.47 | 53615.21 | 0.76 |
| 2 | n.a. | 8.97 | 7952.81 | 0.11 |
| 3 | n.a. | 10.78 | 5951.77 | 0.08 |
| 4 | n.a. | 17.47 | 15229.68 | 0.22 |
| 5 | n.a. | 18.01 | 110955.75 | 1.57 |
| 6 | n.a. | 18.84 | 5302.10 | 0.08 |

TABLE 4-continued

HPLC of product of Example 5 process

| No. | Peak Name | Ret. Time min | Area mAU*min | Rel. Area % |
|---|---|---|---|---|
| 7 | n.a. | 19.10 | 7257.12 | 0.10 |
| 8 | n.a. | 19.84 | 8188.45 | 0.12 |
| 9 | n.a. | 20.16 | 6944.33 | 0.10 |
| 10 | ISR-2 | 20.46 | 6717762.27 | 95.26 |
| 11 | n.a. | 21.52 | 5261.84 | 0.07 |
| 12 | n.a. | 24.67 | 10727.96 | 0.15 |
| 13 | n.a. | 27.26 | 5977.49 | 0.08 |
| 14 | n.a. | 34.64 | 66383.49 | 0.94 |
| 15 | n.a. | 35.62 | 24514.71 | 0.35 |

TABLE 5

HPLC of product of Example 5A process

| No. | Peak Name | Ret. Time min | Area mAU*min | Rel. Area % |
|---|---|---|---|---|
| 1 | n.a. | 5.33 | 53246.31 | 1.04 |
| 2 | n.a. | 5.48 | 61723.88 | 1.21 |
| 3 | n.a. | 6.53 | 17947.74 | 0.35 |
| 4 | n.a. | 8.96 | 25037.14 | 0.49 |
| 5 | n.a. | 16.17 | 112660.36 | 2.21 |
| 6 | n.a. | 17.45 | 209546.25 | 4.11 |
| 7 | n.a. | 18.02 | 79076.72 | 1.55 |
| 8 | n.a. | 18.87 | 108952.66 | 2.14 |
| 9 | ISR-2 | 20.52 | 4286448.20 | 84.10 |
| 10 | n.a. | 21.52 | 38106.23 | 0.75 |
| 11 | n.a. | 24.67 | 65230.24 | 1.28 |
| 12 | n.a. | 27.26 | 30873.05 | 0.61 |
| 13 | n.a. | 36.06 | 8184.13 | 0.16 |

TABLE 6

HPLC of product of Example 26 process

| No. | Peak Name | Ret. Time min | Area mAU*min | Rel. Area % |
|---|---|---|---|---|
| 1 | n.a. | 5.34 | 44058.53 | 0.96 |
| 2 | n.a. | 5.48 | 46725.20 | 1.02 |
| 3 | n.a. | 6.52 | 8674.48 | 0.19 |
| 4 | n.a. | 8.96 | 11880.56 | 0.26 |
| 5 | n.a. | 16.16 | 121866.64 | 2.66 |
| 6 | n.a. | 17.45 | 192015.07 | 4.20 |
| 7 | n.a. | 18.01 | 59547.57 | 1.30 |
| 8 | n.a. | 18.87 | 52749.09 | 1.15 |
| 9 | ISR-2 | 20.53 | 3988963.45 | 87.18 |
| 10 | n.a. | 24.66 | 8829.51 | 0.19 |
| 11 | n.a. | 26.56 | 8216.77 | 0.18 |
| 12 | n.a. | 27.26 | 5790.12 | 0.13 |
| 13 | n.a. | 34.64 | 26342.11 | 0.58 |

In summary, using identical HPLC conditions, irbesartan hydrochloride having a purity of 95.26% is produced according to the process of the present invention, irbesartan having a purity of 87.18% is produced according to the WO2004/007482 process, and irbesartan having a purity of 84.10% is produced in a similar manner to the present invention, but with an added isolation step (i.e. a non-one-pot process). Thus, the process of the present invention represents a simple and highly effective method of producing irbesartan hydrochloride, and irbesartan free base, having a high yield and purity.

It will be appreciated that the invention may be modified within the scope of the appended claims.

The invention claimed is:

1. A process for the preparation of irbesartan hydrochloride of formula (I)

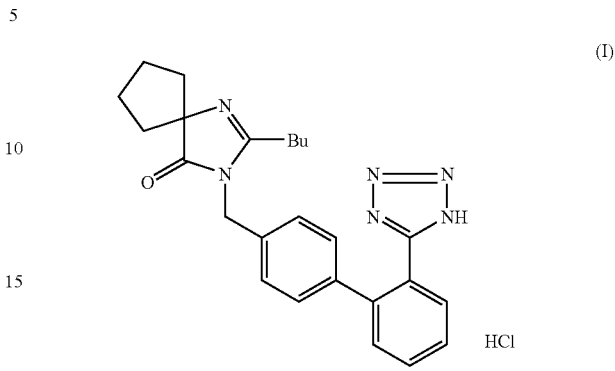

comprising reacting intermediate compounds 2n-butyl-1,3-diazaspiro [4,4] non-1-en-4-one of formula (II), optionally in salt form, and 5-(4'-bromomethyl-biphenyl-2-yl)-1-trityl-1 H-tetrazole of formula (III)

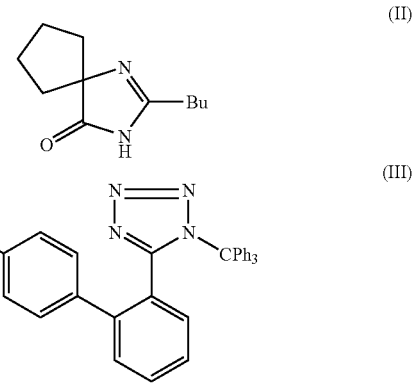

where Hal represents bromo, chloro, fluoro or iodo, wherein reaction of intermediate compounds of formulae (II) and (III) results in formation of intermediate compound 2n-butyl-3[2' (triphenyl methyl tetrazol-5yl)-biphenyl-4-yl-methyl]-1,3-diazaspiro [4,4] non-1-en-4-one (trityl irbesartan) of formula (IV), optionally in salt form, which is subsequently detritylated, and, if necessary, converted to the hydrochloride salt, to yield irbesartan hydrochloride of formula (I)

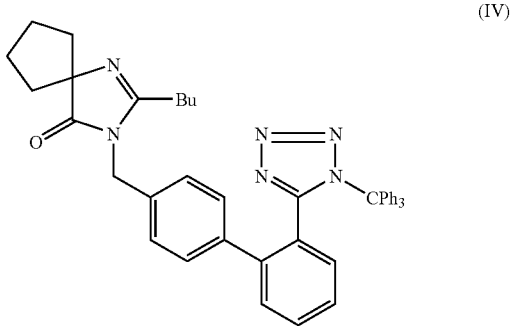

wherein the trityl irbesartan (IV) is not isolated before detritylation, and wherein trityl irbesartan (IV) is formed in the absence of an azide source.

2. The process according to claim 1, wherein Hal represents bromo.

3. The process according to claim 1, wherein an intermediate compound of formula (II) is employed in salt form.

4. The process according to claim 3, wherein said intermediate compound of formula (II) is employed as the hydrochloride.

5. The process according to claim 1, wherein condensation of intermediate compounds of formulae (II) and (III) is carried out at a temperature from about 20° C. to about 95° C.

6. The process according to claim 5, wherein condensation of intermediate compounds of formulae (II) and (III) is carried out at a temperature of about 85° C.

7. The process according to claim 1, which yields irbesartan hydrochloride in one of the following forms: sesquihydrate, hemihydrate, anhydrous or amorphous.

8. The process according to claim 1, which is carried out in the presence of a phase transfer catalyst.

9. The process according to claim 8, wherein said phase transfer catalyst is selected from the group consisting of quaternary ammonium compounds, quaternary phosphonium compounds and crown ethers.

10. The process according to claim 1, which comprises an aromatic or aliphatic hydrocarbon as a solvent of the reaction system.

11. The process according to claim 10, wherein said solvent is selected from the group consisting of benzene, toluene, o-xylene, m-xylene, acetone and MIBK.

12. The process according to claim 1, wherein said reaction system comprises first and second solvent phases.

13. The process according to claim 12, wherein said first solvent phase comprises a hydrocarbon solvent, and said solvent of said second solvent phase is substantially immiscible therewith.

14. The process according to claim 13, wherein said solvent of said second solvent phase comprises water.

15. The process according to claim 1, wherein an inorganic base is present in the reaction system.

16. The process according to claim 15, wherein said inorganic base is selected from the group consisting of hydroxides, carbonates and alkoxides of alkali metals.

17. The process according to claim 16, wherein said inorganic base is selected from the group consisting of KOH, NaOH, LiOH, $K_2CO_3$, $Na_2CO_3$, $Cs_2CO_3$, sodium methoxide, sodium t-butoxide and potassium t-butoxide.

18. The process according to claim 15, wherein said base is employed in powder form.

19. The process according to claim 12, wherein an inorganic base is combined with the solvent of the second solvent phase of the reaction system.

20. The process according to claim 19, wherein said base is selected from the group consisting of KOH, NaOH, LiOH, $K_2CO_3$, $Na_2CO_3$, $Cs_2CO_3$, sodium methoxide, sodium t-butoxide and potassium t-butoxide and is combined with water as the solvent of the second solvent phase of the reaction system.

21. The process according to claim 1, wherein detritylation is achieved by using a mineral acid.

22. The process according to claim 1, which comprises directly isolating irbesartan hydrochloride after detritylation.

23. The process according to claim 1, wherein irbesartan hydrochloride is further purified by dissolving in a solvent at elevated temperature and precipitated with a non-solvent.

24. The process according to claim 23, wherein said solvent is methanol.

25. The process according to claim 23, wherein said non-solvent is ethyl acetate.

26. The process according to claim 1, wherein irbesartan hydrochloride is further purified by suspending in a solvent at elevated temperature and filtering the suspension at room temperature.

27. The process according to claim 26, wherein said solvent is ethyl acetate or isopropyl acetate.

28. The process according to claim 1, wherein the irbesartan hydrochloride is in the sesquihydrate form, and the sesquihydrate is subsequently repeatedly stirred in a solvent at elevated temperature and precipitated with a non-solvent to yield the anhydrous form of irbesartan hydrochloride.

29. The process according to claim 28, wherein the solvent is methanol or a methanol-ethylacetate mixture.

30. The process according to claim 28, wherein the non-solvent is ethyl acetate.

31. The process according to claim 1, further comprising drying the hydrated product at elevated temperature to yield the anhydrous form of irbesartan hydrochloride.

32. The process according to claim 31, wherein the elevated temperature is from 80 to 85° C.

33. The process according to claim 1, further comprising drying the irbesartan hydrochloride product at elevated temperature to yield amorphous irbesartan hydrochloride.

34. The process according to claim 33, wherein the elevated temperature is from 90 to 105° C.

35. The process according to claim 1, which further comprises converting irbesartan hydrochloride prepared thereby to irbesartan free base.

36. The process according to claim 35, which comprises addition of a base.

37. The process according to claim 36, wherein said base comprises aqueous ammonia.

38. The process of claim 1 wherein the reacting of intermediate compounds 2n-butyl-1,3-diazaspiro [4,4] non-1-en-4-one of formula (II), optionally in salt form, and 5-(4'-bromomethyl-biphenyl-2-yl)-1-trityl-1H-tetrazole of formula (III) and detritylation of 2n-butyl-3-[2'(triphenyl methyl tetrazol-5yl)-biphenyl-4-yl-methyl]-1,3-diazaspiro [4,4] non-1-en-4-one (trityl irbesartan) is carried out in a single vessel.

39. The process of claim 1 wherein the step of converting the trityl ibersartan (IV) to irbesartan hydrochloride (I) is carried out in the same solvent or solvents as the step of forming the trityl irbesartan.

40. The process of claim 1 wherein the reacting of intermediate compounds 2n-butyl-1,3-diazaspiro [4,4] non-1-en-4-one of formula (II), optionally in salt form, and 5-(4'-bromomethyl-biphenyl-2-yl)-1-trityl-1H-tetrazole of formula (III) and detritylation of 2n-butyl-3-[2'(triphenyl methyl tetrazol-5yl) -biphenyl-4-yl-methyl]-1,3-diazaspiro [4,4] non-1-en-4-one (trityl irbesartan) is carried out in a single vessel and wherein the step of converting the trityl ibersartan (IV) to irbesartan hydrochloride (I) is carried out in the same solvent or solvents as the step of forming the trityl irbesartan.

* * * * *

UNITED STATES PATENT AND TRADEMARK OFFICE
CERTIFICATE OF CORRECTION

PATENT NO.         : 7,799,928 B2
APPLICATION NO.    : 11/718059
DATED              : September 21, 2010
INVENTOR(S)        : Srinivas L. Pathi et al.

It is certified that error appears in the above-identified patent and that said Letters Patent is hereby corrected as shown below:

Column 16, Line 57, Replace "183.0 g" with -- 83.0 g --

Signed and Sealed this

Sixteenth Day of November, 2010

David J. Kappos
*Director of the United States Patent and Trademark Office*